United States Patent [19]

Zelle et al.

[11] Patent Number: 5,780,484

[45] Date of Patent: Jul. 14, 1998

[54] METHODS FOR STIMULATING NEURITE GROWTH WITH PIPERIDINE COMPOUNDS

[75] Inventors: Robert E. Zelle, Stow; Michael Su, Newton, both of Mass.

[73] Assignee: Vertex Pharmaceuticals Incorporated, Cambridge, Mass.

[21] Appl. No.: 749,114

[22] Filed: Nov. 13, 1996

[51] Int. Cl.$^6$ ............. A61K 31/445; A61K 31/535; A61K 31/47; A61K 38/18

[52] U.S. Cl. ............. 514/316; 514/317; 514/318; 514/237.2; 514/314; 514/12

[58] Field of Search ............. 514/316, 317, 514/318, 237.2, 314, 12

[56] References Cited

U.S. PATENT DOCUMENTS

| | | | |
|---|---|---|---|
| 5,543,423 | 8/1996 | Zelle et al. | 514/332 |
| 5,614,547 | 3/1997 | Hamilton et al. | 514/423 |

FOREIGN PATENT DOCUMENTS

| | | |
|---|---|---|
| WO 96/15101 | 5/1996 | WIPO |
| WO 96/40140 | 12/1996 | WIPO |
| WO 96/40633 | 12/1996 | WIPO |
| WO 97/16190 | 5/1997 | WIPO |

OTHER PUBLICATIONS

J.P. Steiner et al., "High brain densities of the immunophilin FKBP colocalized with calcineurin," *Nature*, 358, pp. 584–587 (1992).

J.R. Hauske et al., "Design and synthesis of novel FKBP inhibitors," *J. Med. Chem.*, 35, pp. 4284–4296 (1992).

B.G. Gold et al., "FK506, an immunosuppressant, increases function recovery and axonal regeneration in the rat following axotomy of the sciatic nerve," *Soc. Neurosci. Abs.*, 19, p. 1316 (1993).

B.G. Gold et al., "The immunosuppressant FK506 increases the Rate of Axonal Regeneration in Rat Sciatic Nerve," *J. Neuroscience*, 15(11), pp. 7509–7516 (Nov., 1995).

W.E. Lyons et al., "Immunosupressant FK506 promotes neurite outgrowth in cultures of PC12 cells and sensory ganglia," *Proc. Natl. Acad. Sci. USA*, 91, pp. 3191–3195 (Apr., 1994).

John Sharkey et al., "Immunophilins mediate the neuroprotective effects of FK506 in focal cerebral ischaemia," *Nature*, 371, pp. 336–339 (Sep. 22, 1994).

W.E. Lyons et al., "Neuronal regeneration enhances the expression of the immunophilin FKBP-12," *J. Neuroscience*, 15, pp. 2985–2994 (Apr., 1995).

*Primary Examiner*—William R. A. Jarvis
*Attorney, Agent, or Firm*—Fish & Neave; James F. Haley, Jr.; N. Govindaswamy

[57] ABSTRACT

The present invention relates to methods for stimulating the growth of neurites in nerve cells. The methods comprise treating nerve cells with piperidine compounds alone or in combination with a neurotrophic factor, such as nerve growth factor. The methods of this invention can be used to promote repair of neuronal damage caused by disease or physical trauma.

14 Claims, No Drawings

METHODS FOR STIMULATING NEURITE GROWTH WITH PIPERIDINE COMPOUNDS

TECHNICAL FIELD OF THE INVENTION

The present invention relates to methods and pharmaceutical compositions for stimulating the growth of neurites in nerve cells. The compositions comprise a neurotrophic amount of a compound and a neurotrophic factor, such as nerve growth factor (NGF). The methods comprise treating nerve cells with the above compositions or compositions comprising the compound without a neurotropic factor. The methods of this invention can be used to promote repair of neuronal damage caused by disease or physical trauma.

BACKGROUND OF THE INVENTION

Neurological diseases are associated with the death or injury of neuronal cells. The loss of dopaminergic neurons in the substantia nigra is the etiological cause for Parkinson's disease. Although the molecular mechanism of neurodegeneration in Alzheimer's disease is yet to be established, it is clear that brain inflammation, and deposition of beta-amyloid protein and other such agents may inhibit the survival of neurons and mitigate the growth of neurites used for communication between neurons. In patients suffering from brain ischemia or spinal cord injuries, extensive neuronal cell death is observed. Currently, there are no satisfactory treatments for these diseases.

Typical treatment of neurological diseases involves drugs capable of inhibiting neuronal cell death. A more recent approach involves the promotion of nerve regeneration by promoting neurite outgrowth.

Neurite outgrowth, which is critical for the survival of neurons, is stimulated in vitro by nerve growth factors (NGF). For example, Glial Cell Line-Derived Neurotrophic Factor (GDNF) demonstrates neurotrophic activity both, in vivo and in vitro, and is currently being investigated for the treatment of Parkinson's disease. Insulin and Insulin-like growth factors have been shown to stimulate growth of neurites in rat pheochromocytoma PC12 cells and in cultured sympathetic and sensory neurons [Recio-Pinto et al., *J. Neurosci.*, 6, pp. 1211–1219 (1986)]. Insulin and Insulin-like growth factors also stimulate the regeneration of injured motor nerves in vivo and in vitro [Near et al., *PNAS*, pp. 89, 11716–11720 (1992); and Edbladh et al., *Brain Res.*, 641, pp. 76–82 (1994)]. Similarly, fibroblast growth factor (FGF) stimulates neural proliferation [D. Gospodarowicz et al., *Cell Differ.*, 19, p. 1 (1986)] and growth [M. A. Walter et al., *Lymphokine Cytokine Res.*, 12, p. 135 (1993)].

There are, however, several disadvantages associated with the use of nerve growth factors for treating neurological diseases. They do not readily cross the blood-brain barrier. They are unstable in plasma. And they have poor drug delivery properties.

Recently, small molecules have been shown to stimulate neurite outgrowth in vivo. In individuals suffering from a neurological disease, this stimulation of neurite outgrowth protects neurons from further degeneration, and accelerates the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.*, 56, pp. 169–78 (1996); and B. S. McEwen et al., *Brain Res. Dev. Brain. Res.*, 87, pp. 91–95 (1995)]. The progress of Alzheimer's disease is slowed in women who take estrogen. Estrogen is hypothesized to complement NGF and other neurotrophins and thereby help neurons differentiate and survive.

Tacrolimus, an immunosuppressive drug, has been demonstrated to act synergistically with NGF in stimulating neurite outgrowth in PC12 cells as well as sensory ganglia [Lyons et al., *PNAS*, 91, pp. 3191–3195 (1994)]. This compound has also been shown to be neuroprotective in focal cerebral ischemia [J. Sharkey and S. P. Butcher, *Nature*, 371, pp.336–339 (1994)] and to increase the rate of axonal regeneration in injured sciatic nerve [Gold et al., *J. Neurosci.*, 15, pp. 7509–16 (1995)].

Though a wide variety of neurological degenerative disorders may be treated by stimulating neurite outgrowth, there are relatively few agents known to possess these properties. Thus, there remains a great need for new pharmaceutically acceptable compounds and compositions that have the ability to stimulate neurite outgrowth in patients.

SUMMARY OF THE INVENTION

Applicants have solved the above problem by discovering that compounds previously invented by one of the co-applicants for use in reversing multi-drug resistance also surprisingly and unexpectedly possess neurotropic activity. These compounds are disclosed in U.S. Pat. No. 5,543,423 and co-pending U.S. application Ser. No. 08/377,283 the disclosures of which are herein incorporated by reference.

These compounds stimulate neurite outgrowth in the presence of exogenous or endogenous NGF. The compositions disclosed herein comprise a compound from the genera described above and a neuronal growth factor. Methods for stimulating neurite outgrowth disclosed herein employ the above compounds either alone or in combination with a neuronal growth factor. These methods are useful in treating nerve damage caused by various neurological diseases and physical traumas and also in ex vivo nerve regeneration.

DETAILED DESCRIPTION OF THE INVENTION

The present invention provides pharmaceutical compositions which comprise three components. The first component is a compound having the formula (I):

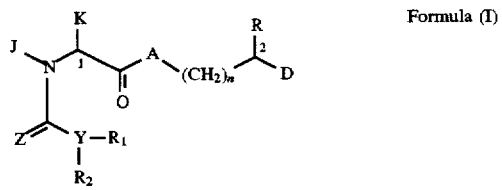

Formula (I)

and pharmaceutically acceptable derivatives thereof, wherein A is $CH_2$ oxygen, $NR_1$;

wherein $R_1$, B and D are independently:

Ar, (C1–C6)-straight or branched alkyl, (C2–C6)-straight or branched alkenyl or alkynyl, (C5–C7)-cycloalkyl substituted ($C_1$–C6)-straight or branched alkyl, (C3–C6)-straight or branched alkenyl or alkynyl, (C5–C7)-cycloalkenyl substituted (C1–C6)-straight or branched alkyl, (C3–C6)-straight or branched alkenyl or alkynyl, Ar-substituted (C1–C6)-straight or branched alkyl, or Ar-substituted (C3–C6)-straight or branched alkenyl or alkynyl, wherein any one of the $CH_2$ groups of said alkyl chains is optionally replaced by a heteroatom selected from the group consisting of O, S, SO, $SO_2$, and NR, wherein R is selected from hydrogen, (C1–C4)-straight or branched alkyl, (C3–C4)-straight or branched alkenyl or alkynyl, or (C1–C4) bridging alkyl wherein a bridge is formed between the nitrogen and a carbon atom of said heteroatom containing chain to form a ring, and wherein said ring is optionally fused to an Ar group;

J is selected from hydrogen, (C1–C6)-straight or branched alkyl, (C3–C6)-straight or branched alkenyl, or —CH$_2$Ar;

K is selected from (C1–C4)-straight or branched alkyl, —CH$_2$Ar, or cyclohexylmethyl;

or J and K are taken together to form a 5–7 membered heterocyclic ring which optionally contains a heteroatom selected from O, S, SO or SO$_2$;

Z is O or S;

Y is O or N, wherein,
when Y is O, then R$_1$ is a lone pair (as used herein, the term "lone pair" refers to a lone pair of electrons, such as the lone pair of electrons present on divalent oxygen) and R$_2$ is selected from Ar, (C1–C6)-straight or branched alkyl, or (C3–C6)-straight or branched alkenyl or alkynyl; and when Y is N, then R$_1$ and R$_2$ are independently selected from Ar, (C1–C6)-straight or branched alkyl, or (C3–C6)-straight or branched alkenyl or alkynyl; or R$_1$ and R$_2$ are taken together to form a heterocyclic 5–6 membered ring selected from pyrrolidine, imidazolidine, pyrazolidine, piperidine, or piperazine;

wherein Ar is selected from phenyl, 1-naphthyl, 2-naphthyl, indenyl, azulenyl, fluorenyl, or anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

wherein Ar optionally contains one to three substituents which are independently selected from hydrogen, halogen, hydroxyl, nitro, —SO$_3$H, trifluoromethyl, trifluoromethoxy, (C1–C6)-straight or branched alkyl, (C2–C6)-straight or branched alkenyl, O-[(C1–C6)-straight or branched alkyl], O-[(C3–C4)-straight or branched alkenyl], O-benzyl, O-phenyl, 1,2-methylenedioxy, —NR$_3$R$_4$, carboxyl, N-(C1–C5-straight or branched alkyl or C3–C5-straight or branched alkenyl) carboxamides, N,N-di-(C1–C5-straight or branched alkyl or C3–C5-straight or branched alkenyl) carboxamides, morpholinyl, piperidinyl, O—Z, CH$_2$—(CH$_2$)$_q$—Z, O—(CH$_2$)$_q$—Z, (CH$_2$)$_q$—O—Z, or CH=CH—Z;

wherein R$_3$ and R$_4$ are independently selected from (C1–C6)-straight or branched alkyl, (C3–C6)-straight or branched alkenyl, hydrogen or benzyl; or wherein R$_3$ and R$_4$ are taken together to form a 5–6 membered or a 8–11 membered heterocyclic ring such as, for example, piperidinyl, morpholinyl or pyrrolidinyl;

wherein Z is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

wherein q is 0–2; and n is 0 or 1.

As used herein for R$_3$ and R$_4$, the term "heterocyclic" refers to a stable 5–6 membered monocycle or 8–11 membered bicyclic heterocycle which is either saturated or unsaturated, and which may be optionally benzofused if monocyclic. Each heterocycle consists of carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. The heterocyclic ring may be attached by any heteroatom of the cycle which results in the creation of a stable structure. Typical examples of such heterocycles include piperidinyl, morpholinyl or pyrrolidinyl.

Preferably, at least one of B or D is independently a straight chain terminated by an aryl group, i.e., a group represented by the formula —(CH$_2$)$_r$—(X)—(CH$_2$)$_s$—Ar, wherein r is 1–4;

s is 0–1;

Ar is as defined above; and each X is independently selected from CH$_2$, O, S, SO, SO$_2$, or NR, wherein R is selected from hydrogen, (C1–C4)-straight or branched alkyl, (C3–C4)-straight or branched alkenyl or alkynyl, or (C1–C4) bridging alkyl wherein a bridge is formed between the nitrogen atom and the Ar group.

The preferred Ar groups of this invention include phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl. Ar groups may contain one to three substituents which are independently selected from hydrogen, hydroxyl, nitro, trifluoromethyl, (C1–C6)-straight or branched alkyl, O-[(C1–C6)-straight or branched alkyl], halogen, SO$_3$H, or NR$_3$R$_4$, wherein R$_3$ and R$_4$ are as defined above.

The compounds of this invention include all optical and racemic isomers.

A "pharmaceutically acceptable derivative," as used herein denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote or augment neurite outgrowth.

According to a preferred embodiment, the pharmaceutical compositions of the present invention comprise a compound having formula (II):

Formula (II)

and pharmaceutically acceptable derivatives thereof, wherein R$_1$, R$_2$, Y, w, and Ar are as defined above.

According to another preferred embodiment, the pharmaceutical compositions of the present invention comprise a compound of formula (III):

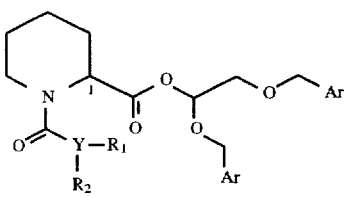
Formula (III)

and pharmaceutically acceptable derivatives thereof, wherein $R_1$, $R_2$, Y, w, and Ar are as defined above.

According to yet another preferred embodiment, the pharmaceutical compositions of the present invention comprise a compound of formula (IV):

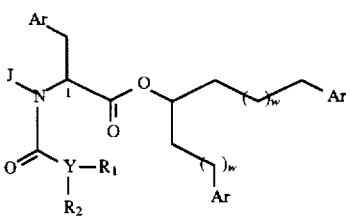
Formula (IV)

and pharmaceutically acceptable derivatives thereof, wherein $R_1$, $R_2$, Y, w, and Ar are as defined above, and J is hydrogen, (C1–C6)-straight or branched alkyl, or (C3–C6)-straight or branched alkenyl.

According to another preferred embodiment, the pharmaceutical compositions of the present invention comprise a compound of formula (V):

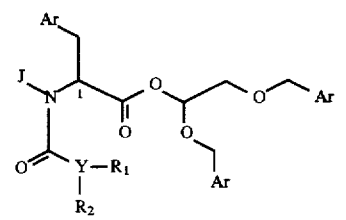
Formula (V)

and pharmaceutically acceptable derivatives thereof, wherein $R_1$, $R_2$, Y, w, and Ar are as defined above, and J is hydrogen, (C1–C6)-straight or branched alkyl, or (C3–C6)-straight or branched alkenyl.

If pharmaceutically acceptable salts of the compounds are used, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The second component in each of the pharmaceutical compositions described above is a neurotrophic factor. The term "neurotrophic factor", as used herein, refers to compounds which are capable of stimulating growth or proliferation of nervous tissue. As used in this application, the term "neurotrophic factor" excludes the compounds described herein.

Numerous neurotrophic factors have been identified in the art and any of those factors may be utilized in the compositions of this invention. These neurotrophic factors include, but are not limited to, nerve growth factor (NGF), insulin growth factor (IGF-1) and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). The most preferred neurotrophic factor in the compositions of this invention is NGF.

The third component of the pharmaceutically acceptable compositions of this invention is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both, the compound and the neurotrophic factor that may be combined with the carrier materials to produce a single dosage form will vary depending upon the host treated, the particular mode of administration. The two active ingredients of the pharmaceutical compositions of this invention act synergistically to stimulate neurite outgrowth. Therefore, the amount of neurotrophic factor in such compositions will be less than that required in a monotherapy utilizing only that factor. Preferably, the compositions should be formulated so that a dosage of between 0.01–100 mg/kg body weight/day of the compound can be administered and a dosage of between 0.01–100 µg/kg body weight/day of the neurotrophic can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and neurotrophic factor in the composition.

According to another embodiment, this invention provides methods for stimulating neurite outgrowth. In one aspect of this embodiment, the method is used to stimulate neurite outgrowth in a patient and is achieved by administering to the patient a pharmaceutically acceptable composition comprising any of the compounds described above and a pharmaceutically acceptable carrier. The amount of compound utilized in these methods is between about 0.01 and 100 mg/kg body weight/day.

In another aspect of this embodiment, the method is used to stimulate nerve growth ex vivo. For this aspect, the compounds described above can be applied directly to the nerve cells in culture. This aspect of the invention is useful for ex vivo nerve regeneration.

According to an alternate embodiment, the method of stimulating neurite outgrowth comprises the additional step of treating a patient or ex vivo nerve cells in culture with a neurotrophic factor, such as those contained in the pharmaceutical compositions of this invention described above. This embodiment includes administering the compound and the neurotrophic agent in a single dosage form or in separate, multiple dosage forms when they are to be administered to a patient. If separate dosage forms are utilized, they may be administered concurrently, consecutively or within less than about 5 hours of one another.

The methods and compositions of this invention may be used to treat nerve damage caused by a wide variety of diseases or physical traumas. These include, but are not limited to, Alzheimer's disease, Parkinson's disease, ALS, multiple sclerosis, stroke and ischemia associated with stroke, neural paropathy, other neural degenerative diseases, motor neuron diseases, sciatic crush, peripheral neuropathy, particularly neuropathy associated with diabetes, spinal cord injuries and facial nerve crush.

In order that the invention described herein may be more fully understood, the following examples are set forth. It should be understood that these examples are for illustrative purposes only and are not to be construed as limiting this invention in any manner.

EXAMPLES

General Methods

Proton nuclear magnetic resonance ($^1$H NMR) spectra were recorded at 500 MHz on a Bruker AMX 500. Chemical

9 shifts are reported in parts per million (δ) relative to Me₄Si (δ 0.0). Analytical high performance liquid chromatography was performed on either a Waters 600E or a Hewlett Packard 1050 liquid chromatograph.

Example 1
1,7-Dipyridin-3-yl-hept-1,6-diyne-4-ol (1):

A mixture of 1,6-heptadiyn-4-ol (25 g, 0.231 mol), palladium(II) acetate (2.6 g, 11.0 mmol), copper(I)iodide (3.3 g, 11.0 mmol) and triphenylphosphine (9.1 g, 35.0 mmol) in degassed triethylamine (300 mL) was treated with 3-bromopyridine (77 g, 0.49 mol). After stirring for 24 h at room temperature, the reaction was filtered through a plug of Celite and the Celite washed with ethyl acetate (EtOAc). The filtrate was concentrated to afford a dark brown oil. This material was dissolved in 2N hydrochloric acid (HCl) and washed with EtOAc (2×). The pH of the aqueous layer was adjusted to pH>8 by addition of 3N sodium hydroxide (NaOH) and then extracted with EtOAc (2×). The extracts were combined, washed with half-saturated aqueous sodium chloride, brine, dried over magnesium sulfate (MgSO₄), filtered and concentrated. The residue was passed through a plug of silica gel (SiO₂), elution with EtOAc to provide 33.1 g of compound 1 as a solid upon drying.

Example 2
1,7-Dipyridin-3-yl-heptan-4-ol (2):

A suspension of platinum oxide (280 mg) in absolute ethanol (1 mL) was diluted with absolute methanol (10 mL) followed by the addition of compound 1 (2.81 g, 10.73 mmol). The suspension was placed under 40 psi of hydrogen gas. After hydrogen consumption ceased, the hydrogen was replaced with nitrogen and the reaction was filtered and concentrated to provide 2.87 g of compound 2 as a viscous oil.

Example 3
(S)-Piperidine-1,2-dicarboxylic acid 1-tert-butyl ester2-(1-(3-pyridin-3-yl-propyl)-4-pyridin-3-yl)-butyl ester (3):

To a solution of compound 2 (9.5 g, 35.18 mmol) and (S)-piperidine-1,2 dicarboxylic acid 1-tert-butyl ester (12.1 g, 52.78 mmol), and N,N-dimethyl-4-aminopyridine (427 mg, 3.5 mmol) in methylene chloride (CH₂Cl₂, 50 mL) at 0° C. was added 1-(3-dimethylamino-propyl)-3-ethylcarbodiimide hydrochloride (10.1 g, 52.78 mmol). The reaction was warmed to room temperature and allowed to stir for 16 h. The reaction was diluted with EtOAc, washed with water, 5% aqueous sodium bicarbonate (NaHCO₃), brine, dried over anhydrous magnesium sulfate (MgSO₄) and concentrated to provide 16.67 g of compound 3 as a viscous oil.

Example 4
(S)-Piperidine-2-carboxylic acid 2-(1-(3-pyridin-3-yl-propyl)-4-pyridin-3-yl)-butyl ester (4):

To a solution of compound 3 (16.67 g, 34.66 mmol) in CH₂Cl₂ (40 mL) at 0° C. was added trifluoroacetic acid (40 mL). After the addition was complete, the reaction was warmed to room temperature and stirred for 4 h. The reaction was concentrated and the residue taken up into water and made basic with solid K₂CO₃. The product was extracted with CH₂Cl₂(2×). The extracts were combined dried over MgSO₄, filtered and concentrated to provide 13.20 g of compound 4 as a viscous oil.

Example 5
(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester (5):

10

To a mixture of N-methyl-3,4,5-trimethoxyaniline (130 mg, 0.66 mmol) and diisoproylethylamine (i-Pr₂NEt, 215 μL, 1.2 mmol) in methylene chloride (CH₂Cl₂, 1 mL) was added 1.2M phosgene in toluene (1.65 mL). After stirring for 2 h, the reaction was concentrated and placed under vacuum to remove residual phosgene. To a solution of compound 4 (225 mg, 0.59 mmol) in CH₂Cl₂ (1.5 mL) containing i-Pr₂EtN (215 μL, 1.2 mmol) was added the above preformed acyl chloride in CH₂Cl₂ (1.5 mL). After stirring for 1 h, the reaction was diluted with ethyl acetate (EtOAc), washed with 5% aq. NaHCO₃, brine, dried over MgSO₄, filtered and concentrated in vacuo to provide a viscous oil. Chromatography of the residue on SiO₂ (elution with 30 to 60% acetone:hexanes) provided 238 mg (67%) of compound 5 as a viscous oil. ¹H NMR (500 MHz, CDCL₃) δ 8.44–8.40 (m, 4H), 7.35 (m, 2H), 7.22–7.18 (m, 2H), 6.43 (br s, 2H), 4.98 (m, 1H), 4.74 (m, 1H), 3.84 (s, 9H), 3.42 (br s, 1H), 3.18 (s, 3H), 2.92 (m, 1H), 2.65–2.56 (m, 5H), 2.06–1.98 (m, 1H), 1.70–153 (m, 15H).

Example 6
(S)-1-((3-Trifluoromethylphenyl)-methyl-carbamoyl)-piperidine-2-carboxylic acid 4-pyridin-3-yl-1-(3-pyridin-3-yl-propyl)-butyl ester (6):

Compound 6 was prepared according to the protocol of Example 5, except that N-methyl-3,4,5-trimethoxyaniline was replaced with N-methyl-3-trifluoromethylaniline. ¹NMR (500 MHz, CDCl₃) δ 8.42–8.39 (m, 4H), 7.50–6.16 (m, 10H), 4.99 (m, 1H), 4.64 (m, 1H), 3.29 (m, 1H), 3.20 (s, 3H), 2.93 (m, 1H), 2.67–2.53 (m, 4H), 2.03–1.99 (m, 1H), 1.69–1.53 (m, 13H).

Example 7
(S)-1-((4-Tert-butylphenyl)-methyl-carbamoyl)-piperidine-2-carboxylic acid 4-pyridin-3-yl-1-(3-pyridin-3-yl-propyl)-butyl ester (7):

Compound 7 was prepared according to the protocol of Example 5, except that N-methyl-3,4,5-trimethoxyaniline was replaced with N-methyl-4-tert-butylaniline. ¹NMR (500 MHz, CDCl₃) δ 8.40 (m, 4H), 7.49–7.42 (m, 2H), 7.30 (d, 2H), 7.17 (m, 2H), 7.05 (d, 2H), 4.99 (m, 1H), 4.64 (m, 1H), 3.35 (m, 1H), 3.14 (s, 3H), 2.84 (dt, 1H), 2.64–2.52 m, 4H), 2.00–1.95 (m, 1H), 1.70–1.48 (m, 11H), 1.27 (s, 9H), 1.20–1.02 (m, 2H).

Example 8
(S)-1-((4-Isopropylphenyl)-methyl-carbamoyl)-piperidine-2-carboxylic acid 4-pyridin-3-yl-1-(3-pyridin-3-yl-propyl)-butyl ester (8):

Compound 8 was prepared according to the protocol of Example 5, except that N-methyl-3,4,5-trimethoxyaniline was replaced with N-methyl-4-iso-propylaniline. ¹H NMR (500 MHz, CDCl₃) δ 8.42–8.39 (m, 4H), 7.49–7.43 (m, 2H), 7.18 (m, 2H), 7.14 (d, 2H), 7.06 (d, 2H), 4.99 (m, 1H), 4.64 (m, 1H), 3.35 (br d, 1H), 3.15 (s, 3H), 2.85 (m, 2H), 2.59 (m, 4H), 1.97 (m, 1H), 1.70–1.49 (m, 11H), 1.21 (d, 6H), 1.20–1.02 (m, 2H).

Example 9
(S)-1-(Piperidine-1-carbonyl)-piperidine-2-carboxylic acid 4-pyridin-3-yl-1-(3-pyridin-3-yl-propyl)-butyl ester (9):

Compound 9 was prepared according to the protocol of Example 5, except that N-methyl-3,4,5-trimethoxyaniline was replaced with N-piperidine. ¹H NMR (500 MHz, CDCl₃) δ 8.42–8.39 (m, 4H), 7.50–7.43 (m, 2H), 7.24–7.16 (m, 2H), 4.98 (m, 1H), 4.67 (t, 1H), 3.32–3.09 (m, 8H), 2.64–2.52 (m, 6H), 2.01–1.96 (m, 1H), 1.80–1.30 (m, 15H).

Example 10
(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester (10):

Compound 10 was prepared according to the protocols of Examples 1–5, except that 3-bromopyridine was replaced with 1-bromopyridine. $^1$H NMR (500 MHz, CDCl$_3$) δ 8.50 (t, 2H), 7.56 (dq, 2H), 7.18–7.08 (m, 4H), 6.43 (s, 2H), 4.97 (q, 1H), 4.78 (m, 1H), 3.83 (s, 9H), 3.44 (br d, 1H), 3.19 (s, 3H), 2.89 (dt, 1H), 2.82–2.73 (m, 4H), 2.07 (br d, 1H), 1.81–1.52 (m, 12H).

Example 11
(S)-Piperidine-1,2-dicarboxylic acid 1-(3,4,5-trimethoxyphenyl) ester 2-(4-pyridin-3-yl-1-(3-pyridin-3-yl-propyl)-butyl) ester (11):

Compound 11 was prepared according to the protocol of Example 5, except that N-methyl-3,4,5-trimethoxyaniline was replaced with 3,4,5-trimethoxyphenol. Compound 11 was obtained as a mixture of rotomers: $^1$H NMR (500 MHz, CDCl$_3$) δ 8.42–8.35 (m), 7.50–7.32 (m), 7.28–7.18 (m), 6.34 (s), 6.27 (s), 5.34–4.90 (m), 4.19–4.01(m), 3.78 (s), 3.75 (s), 3.22 (br dt), 3.14 (quintet), 3.05–2.90 (m), 2.65–2.53 (m), 2.27–2.21 (m), 2.02 (s), 1.80–1.45 (m).

Example 12
(S)-Piperidine-2-carboxylic acid 2-(1-(2-phenyl-ethyl)-3-phenyl-propyl ester (12):

Compound 12 was prepared according to the protocols of Examples 3–4, except that compound 2 in Example 3 was replaced with 1,5-diphenylpentan-3-ol.

Example 13
(S)-1-((3,4,5-Trimethoxyphenyl)-methyl-carbamoyl)-piperidine-2-carboxylic acid 1-(2-phenyl-ethyl)-3-phenyl-propyl ester (13):

Compound 13 was prepared according to the protocol of Example 5, except that compound 4 was replaced with compound 12. $^1$H NMR (500 MHz, CDCl$_3$) δ 7.27 (m, 4H), 7.20–7.14 (m, 6H), 6.47 (s, 2H), 5.01 (m, 1H), 4.87 (m, 1H), 3.84 (s, 6H), 3.83 (s, 3H), 3.48 (br d, 1H), 3.23 (s, 3H), 2.94 (dt, 1H), 2.72–2.44 (m, 4H), 2.17–2.10 (m, 1H), 2.00–1.85 (m, 4H), 1.67–1.60 (m, 2H), 1.45–1.40 (m, 1H), 1.30–1.18 (m, 2H).

Example 14
4-(Methyl-(2-(1-phenethyl-3-phenyl-propoxycarbonyl)-piperidine-1-carbonyl)-amino)-benzenesulfonic acid (14):

Compound 14 was prepared according to the protocol of Example 13, except that N-methyl-3,4,5-trimethoxyaniline was replaced with N-methyl-4-aminophenyl sulfonic acid.

Example 15
(S)-Piperidine-2-carboxylic acid 1-benzyloxymethyl-2-benzyloxyethyl ester (15):

Compound 15 was prepared according to the protocols of Examples 3–4, except that compound 2 in Example 3 was replaced with 1,3-dibenzyloxypropan-2-ol.

Example 16
(S)-1-(Methyl-(4-morpholin-1-yl-phenyl)-carbamoyl)-piperidine-2-carboxylic acid 2-benzyloxy-1-(benzyloxymethyl)-ethyl ester (16):

Compound 16 was prepared according to the protocol of Example 5, except that compound 4 was replaced with compound 15 and N-methyl-3,4,5-trimethoxyaniline with N-methyl-4-morpholinoaniline. $^1$H NMR (500 MHz, CDCl$_3$) δ 7.34–7.11 (m, 10H), 7.09 (d, 2H), 6.84 (d, 2H), 5.29 (quintet, 1H), 4.81 (br t, 1H), 4.54 (d, 2H), 4.49 (dd, 2H), 3.84 (t, 2H), 3.67 (t, 2H), 3.40 (br d, 1H), 3.15 (s, 3H), 3.09 (t, 4H), 2.86 (dt, 1H), 2.08–2.05 (m, 1H), 1.60–1.44 (m, 2H), 1.27–1.08 (m, 3H).

Example 17
(S)-1-(Methyl-(4-piperidin-1-yl-phenyl)-carbamoyl)-piperidine-2-carboxylic acid 2-benzyloxy-1-(benzyloxymethyl)-ethyl ester (17):

Compound 17 was prepared according to the protocol of Example 16, except that N-methyl-3,4,5-trimethoxyaniline was replaced with N-methyl-4-piperdinoaniline. $^1$H NMR (500 MHz, CDCl$_3$) δ 7.36–7.25 (m, 10H), 7.06 (d, 2H), 6.86 (d, 2H), 5.29 (quintet, 1H), 4.79 (m, 1H), 4.55–4.48 (m, 4H), 3.66 (m, 4H), 3.41 (br d, 1H), 3.14 (s, 3H), 3.10 (m, 4H), 2.87 (dt, 1H), 2.05 (br d, 1H), 1.73–1.67 (m, 4H), 1.61–1.45 (m, 4H), 1.25–1.08 (m, 3H).

Example 18
(S)-Piperidine-1,2-dicarboxylic acid 2-(2-benzyloxy-1-(benzyloxymethyl)-ethyl)ester 1-quinolin-5-yl ester (18):

Compound 18 was prepared according to the protocol of Example 16, except that N-methyl-3,4,5-trimethoxyaniline was replaced with 5-hydroxyquinoline. Compound 18 was a mixture of rotomers. $^1$H NMR (500 MHz, CDCl$_3$) δ 8.89 (dd), 8.86 (dd), 8.90 (d), 8.24 (d), 7.89 (t), 7.67 (t), 7.63 (t), 7.36–7.18 (m), 5.44 (quintet), 5.36 (quintet), 5.20 (d), 5.02 (d), 4.56–4.44 (m), 4.34 (br d), 4.14 (br d), 3.72–3.56 (m), 3.39 (dt), 3.09 (dt), 2.38 (br t), 1.90–1.49 (m), 1.40–1.29 (m).

Example 19
(S)-Piperidine-1, 2-dicarboxylic acid 2-(2-benzyloxy-1-(benzyloxymethyl)-ethyl)ester 1-pyridin-3-yl ester (19):

Compound 19 was prepared according to the protocol of Example 16, except that N-methyl-3,4,5-trimethoxyaniline was replaced with 3-hydroxypyridine. Compound 19 was a mixture of rotomers. $^1$H NMR (500 MHz, CDCl$_3$) δ 8.46–8.41 (m), 7.48 (dt), 7.43 (dt), 7.34–7.24 (m), 7.18 (dd), 5.40–5.33 (m), 5.03 (dd), 4.57–4.47 (m), 4.17 (br d), 3.69–3.66 (m), 3.27 (dt), 3.05 (dt), 2.33 (br d), 1.81–1.71 (m), 1.69–1.64 (m), 1.56–1.43 (m), 1.35–1.27(m).

Example 20
2-(1,3-Dimethyl-3(3,4,5-trimethoxyphenyl)ureido)-3 phenyl-propanoic acid 4-pyridin-3-yl-1-(3-pyridin-3-yl-propyl)-butyl ester(20):

Compound 20 is prepared according to the protocols of Examples 3–5, by replacing (S)-piperidine-1,2-dicarboxylic acid 1-tert-butyl ester with N-(tert-butoxycarbonyl)-L-phenylalanine.

Example 21
2-(1,3-Dimethyl-3-(3,4,5-trimethoxyphenyl)ureido)-3-(phenyl)-propanoic acid 3-pyridin-3-yl-1-(2-pyridin-3-yl-ethyl)-propyl ester (21):

Compound 21 is prepared according to the protocols of Examples 3–5, by replacing (S)-piperidine-1,2-dicarboxylic acid 1-tert-butyl ester with N-(tert-butoxycarbonyl)-L-phenylalanine and 1,7-dipyridin-3-yl-heptan-4-ol with 1,5-dipyridin-3-yl-pentan-3-ol.

Example 22
N-Methyl-2-phenylethylamine-1,2-dicarboxylic acid 1-(3,4,5-trimethoxyphenyl) ester 2-(4-pyridin-3-yl-1-(3-pyridin-3-yl-propyl)butyl) ester (22):

Compound 22 is prepared according to the protocol of Example 20, by replacing N-methyl-3,4,5-trimethoxyaniline with 3,4,5-trimethoxyphenol.

Example 23
N-Methyl-2-phenylethylamine-1,2-dicarboxylic acid 1-(3,4,5-trimethoxyphenyl) ester 2-(3-pyridin-3-yl-1-(2-pyridin-3-yl-ethyl)propyl) ester (23):

Compound 23 is prepared according to the protocol of Example 21, by replacing N-methyl-3,4,5-trimethoxyaniline with 3,4,5-trimethoxyphenol.

Example 24

In order to directly determine the neurotrophic activity of compounds described in this invention, the neurite outgrowth assay was carried out with pheochromocytoma PC12 cells as described by Lyons et al. (1994).

PC12 cells are mainatined at 37 degree and 5% CO2 in Dulbecco's modified Eagle's medium (DMEM) suppplemented with 10% heat-inactivated horse serum, 5% heat-inactivated fetal bovine serum (FBS), and 1% glutamate. The cells are then plated at $10^5$ per well in 96 well plates coated with 5μ/cm$^2$ rat tail collagen and allowed to attach overnight. The medium is then replced with DMEM, 2% heat-inactivated horse serum, 1% glutamate, 1-5 ng/ml of NGF (Sigma) and varying concentrations of compound (0.1 nM-10 nM). The background control culture is administered with 105 ng/ml of NGF alone without compound. Positive control cultures are administered with high concentration of NGF (50 ng/ml).

The compounds described in this invention herein cause a significant increase in neurite outgrowth over background control cultures.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A method for stimulating neurite growth in a patient or in an ex vivo nerve cell comprising the step of administering to said patient or said nerve cell a neurotrophic amount of a compound having the formula (I):

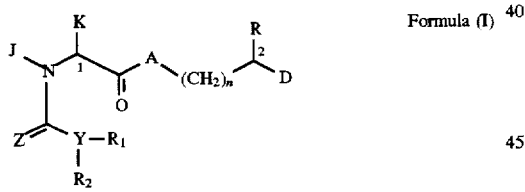

Formula (I)

and pharmaceutically acceptable derivatives thereof, wherein:

A is oxygen;

$R_1$, B and D are independently:

hydrogen, Ar, (C1–C6) straight or branched alkyl, (C2–C6) straight or branched alkenyl or alkynyl, (C5–C7) cycloalkyl-substituted (C1–C6) straight or branched alkyl, (C5–C7) cycloalkyl-substituted (C3–C6) straight or branched alkenyl or alkynyl, (C5–C7) cycloalkenyl-substituted (C1–C6) straight or branched alkyl, (C5–C7) cycloalkenyl-substituted (C3–C6) straight or branched alkenyl or alkynyl, Ar-substituted (C1–C6) straight or branched alkyl, or Ar-substituted (C3–C6) straight or branched alkenyl or alkynyl;

wherein any one of the CH$_2$ groups of said alkyl chain in $R_1$, B and D is optionally replaced by O, S, SO, SO$_2$ or NR;

wherein R is hydrogen, (C1–C4) straight or branched alkyl, (C3–C4) straight or branched alkenyl or alkynyl, or (C1–C4) bridging-alkyl wherein a bridge is formed between the nitrogen and a carbon atom of said alkyl chain to form a ring, and wherein said ring is optionally fused to Ar;

J and K are taken together with the nitrogen and carbon atoms to which they are respectively bound to form a piperidine ring;

Z is O or S;

Y is O or N; wherein when Y is O, then $R_1$ is a lone pair and $R_2$ is selected from Ar, (C1–C6)-straight or branched alkyl, and (C3–C6)-straight or branched alkenyl or alkynyl; and when Y is N, then $R_1$ and $R_2$ are independently selected from the group consisting of Ar, (C1–C6)-straight or branched alkyl, and (C3–C6)-straight or branched alkenyl or alkynyl; or $R_1$ and $R_2$ are taken together to form a heterocyclic 5–6 membered ring selected from the group consisting of pyrrolidine, imidazolidine, pyrazolidine, piperidine, and piperazine;

wherein Ar is a carboxylic aromatic group selected from the group consisting of phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

wherein Ar is optionally substituted with one to three substituents which are independently selected from hydrogen, halogen, hydroxyl, nitro, —SO$_3$H, trifluoromethyl, trifluoromethoxy, (C1–C6)-straight or branched alkyl, (C2–C6)-straight or branched alkenyl, O-[(C1–C6)-straight or branched alkyl], O-[(C3–C4)-straight or branched alkenyl], O-benzyl, O-phenyl, 1,2-methylenedioxy, —NR$_3$R$_4$, carboxyl, N-(C1–C5-straight or branched alkyl or C3–C5-straight or branched alkenyl) carboxamides, N,N-di-(C1–C5-straight or branched alkyl or C3–C5-straight or branched alkenyl) carboxamides, morpholinyl, piperidinyl, O—Z–, CH$_2$—(CH$_2$)$_q$—Z', O-(CH$_2$)$_q$—Z', (CH$_2$)$_q$—Z'—O—Z', or CH=CH—Z';

wherein $R_3$ and R4 are independently selected from (C1–C6)-straight or branched alkyl, (C3–C6) straight or branched alkenyl or alkynyl, hydrogen or benzyl; or wherein $R_3$ and $R_4$ are taken together to form a 5–6 membered heterocyclic ring;

wherein Z' is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

wherein q is 0–2; and n is 0 or 1.

2. The method according to claim 1, wherein said compound is selected from:

(S)-1-((3,4,5-Trimethoxyphenyl)-methyl-carbamoyl) piperidine-2-carboxylic acid 4-pyridin-3-yl-1-(3-pyridin-3-yl-propyl)-butyl ester;

(S)-1-((3-Trifluoromethylphenyl)-methyl-carbamoyl) piperidine-2-carboxylic acid 4-pyridin-3-yl-1-(3-pyridin-3-yl-propyl)-butyl ester;

(S)-1-((4-Tert-butylphenyl)-methyl-carbamoyl) piperidine-2-carboxylic acid 4-pyridin-3-yl-1-(3-pyridin-3-yl-propyl)-butyl ester;

(S)-1-((4-Isopropylphenyl)-methyl-carbamoyl) piperidine-2-carboxylic acid 4-pyridin-3-yl-1-(3-pyridin-3-yl-propyl)-butyl ester;

(S)-1-(Piperidine-1-carbonyl)-piperidine-2-carboxylic acid 4-pyridin-3-yl-1-(3-pyridin-3-yl-propyl)-butyl ester;

(S)-1-((3,4,5-Trimethoxyphenyl)-methyl-carbamoyl) piperidine-2-carboxylic acid 4-pyridin-1-yl-1-(3-pyridin-1-yl-propyl)-butyl ester;

(S)-Piperidine-1,2-dicarboxylic acid 1-(3,4,5-trimethoxyphenyl)ester-2-(4-pyridin-3-yl-1-(3-pyridin-3-yl-propyl)-butyl)ester;

(S)-1-((3,4,5-Trimethoxyphenyl)-methyl-carbamoyl) piperidine-2-carboxylic acid 1-(2-phenyl-ethyl)-3-phenyl-propyl ester;

4-(Methyl-(2-(1-phenethyl-3-phenyl-propoxycarbonyl) piperidine-1-carbonyl)-amino)-benzenesulfonic acid;

(S)-Piperidine-2-carboxylic acid 1-benzyloxy-methyl-2-benzyloxyethyl ester;

(S)-1-(Methyl-(4-morpholin-1-yl-phenyl)-carbamoyl) piperidine-2-carboxylic acid 2-benzyloxy-1-(benzyloxy-methyl)-ethyl ester;

(S)-1-(Methyl-(4-piperidin-1-yl-phenyl)-carbamoyl) piperidine-2-carboxylic acid 2-benzyloxy-1-(benzyloxy-methyl)-ethyl ester;

(S)-Piperidine-1,2-dicarboxylic acid 2-(2-benzyloxy-1-(benzyloxymethyl)-ethyl)ester-1-quinolin-5-yl ester;

(S)-Piperidine-1,2-dicarboxylic acid 2-(2-benzyloxy-1-(benzyloxymethyl)-ethyl)ester-1-pyridin-3-yl ester.

3. The method according to claim 1, wherein, in compound of formula (I), at least one of B or D is independently represented by the formula —(CH$_2$)$_r$—(X)—(CH$_2$)$_s$—Ar, wherein r, s, and X are as defined in claim 2.

4. The method according to claim 1, wherein said compound has formula (II) or formula (III):

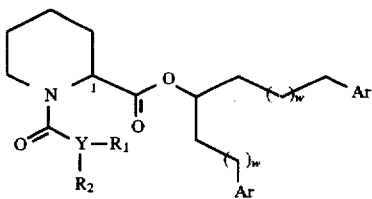

Formula (II)

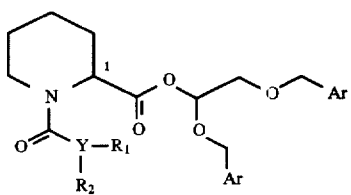

Formula (III)

wherein R$_1$, R$_2$, Y, and Ar are as defined in claim 1, and w is 1 or 2.

5. The method according to any one of claims 3, 4 and 1, wherein Ar is selected from phenyl, 2-pyridyl, 3-pyridyl, 4-pyridyl, indolyl, isoindolyl, quinolinyl, isoquinolinyl, 1,2,3,4-tetrahydroisoquinolinyl, or 1,2,3,4-tetrahydroquinolinyl, wherein Ar optionally contains one to three substituents which are independently selected from hydrogen, hydroxyl, nitro, trifluoromethyl, (C1–C6)-straight or branched alkyl, O-|(C1–C6)-straight or branched alkyl|, halogen, SO$_3$H, and NR$_3$R$_4$.

6. The method according to claim 1, wherein said patient is suffering from Alzheimer's disease, Parkinson's disease, ALS, multiple sclerosis, stroke or ischemia associated with stroke, neural paropathy, other neural degenerative diseases, motor neuron diseases, sciatic crush, peripheral neuropathy, diabetic neuropathy, spinal cord injury or facial nerve crush.

7. The method according to claim 6, further comprising the additional step of administering to said patient a neurotrophic factor either as part of a multiple dosage form with said compound or as a separate dosage form.

8. The method according to claim 7, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotropic factors CNTF), glial cell-derived neurotropic factor (GDNF), neurotrophin-3 (NT-3) and neurotrophin 4/5 (NT-4/5).

9. The method according to claim 8, wherein said neurotrophic factor is nerve growth factor (NGF).

10. The method according to any one of claims 6–9, wherein said patient is suffering from diabetes-associated peripheral neuropathy.

11. The method according to claim 1, wherein said method is used to stimulate ex vivo nerve regeneration.

12. The method according to claim 11, comprising the additional step of contacting said nerve cell with a neurotrophic factor.

13. The method according to claim 12, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotropic factors (CNTF), glial cell-derived neurotropic factor (GDNF), neurotrophin-3 (NT-3) and neurotrophin 4/5 (NT-4/5).

14. The method according to claim 13, wherein said neurotrophic factor is nerve growth factor (NGF).

\* \* \* \* \*

UNITED STATES PATENT AND TRADEMARK OFFICE
CERTIFICATE OF CORRECTION

PATENT NO.    : 5,780,484
DATED         : June 14, 1998
INVENTOR(S)   : Zelle et al.

It is certified that error appears in the above-identified patent and that said Letters Patent is hereby corrected as shown below:

Title page,
Item [56], in W.E. Lyons delete "Immunosupressant" and substitute therefor
-- Immunosuppressant --.

Column 1,
Line 11, delete "neurotropic" and substitute therefore -- neurotrophic --

Column 6,
Line 29, delete "(NT-3)and" and substitute therefore -- (NT-3) and --.

Column 9,
Line 1, delete "(6)" and substitute therefor -- ($\delta$) --.

Column 10,
Line 15, delete "(m. 2H)," and substitute therefor -- (m, 2H) --.
Line 39, delete "(m. 4H)," and substitute therefor -- (m, 4H), --.

Column 13,
Line 10, delete "mainatined" and substitute therefor -- maintained --.
Line 16, delete "replced" and substitute therefor -- replaced --.

Column 14,
Line 49, delete "O-Z-," and substitute therefor -- O-Z'-, --.

Column 15,
Line 41, delete "r, s, and X are as defined in claim 2" and substitute therefor -- r is 1-4; s is 0-1, and each X is independently selected from $CH_2$, O, S, SO, $SO_2$, and NR, wherein R is selected from hydrogen, (C1-C4)-straight or branched alkyl, (C3-C4)-straight or branched alkenyl or alkynyl, or (C1-C4) bridging alkyl wherein a bridge is formed between the nitrogen atom and the Ar group. --.

UNITED STATES PATENT AND TRADEMARK OFFICE
CERTIFICATE OF CORRECTION

PATENT NO. : 5,780,484
DATED : June 14, 1998
INVENTOR(S) : Zelle et al.

It is certified that error appears in the above-identified patent and that said Letters Patent is hereby corrected as shown below:

Column 16,
Line 31, delete both occurrences of "neurotropic" and substitute therefor -- neurotrophic --.
Line 53 and 54, delete "neurotropic" and substitute therefor -- neurotrophic --.
Line 55, delete "and" and substitute therefor -- or --.

Signed and Sealed this

Thirteenth Day of November, 2001

Attest:

NICHOLAS P. GODICI
Attesting Officer  Acting Director of the United States Patent and Trademark Office